(12) United States Patent
Smith et al.

(10) Patent No.: US 7,105,642 B2
(45) Date of Patent: Sep. 12, 2006

(54) MONOCLONAL ANTIBODIES SPECIFIC FOR PHOSPHORYLATED ESTROGEN RECEPTOR ALPHA (SER118) AND USES THEREOF

(75) Inventors: Bradley L. Smith, Marblehead, MA (US); Katherine Crosby, Middleton, MA (US); Jiong Wu, Salem, MA (US)

(73) Assignee: Cell Signalling Technology, Inc., Danvers, MA (US)

( * ) Notice: Subject to any disclaimer, the term of this patent is extended or adjusted under 35 U.S.C. 154(b) by 665 days.

(21) Appl. No.: 10/211,613

(22) Filed: Aug. 2, 2002

(65) Prior Publication Data

US 2003/0099641 A1    May 29, 2003

Related U.S. Application Data

(60) Provisional application No. 60/310,066, filed on Aug. 3, 2001.

(51) Int. Cl.
*C07K 5/06* (2006.01)
*C12N 5/16* (2006.01)

(52) U.S. Cl. .................... 530/388.1; 435/326; 435/331

(58) Field of Classification Search ............. 530/387.1, 530/388.1; 325/326, 330; 435/810, 326, 435/331
See application file for complete search history.

(56) References Cited

OTHER PUBLICATIONS

Kobayashi et al., Breast Cancer 7(2): 136-141 (2000).
Osborne et al., *Clin. Cancer* 7(12): 4338s-4342s (2001).
Beato et al., *Cell* 83: 851-857 (1995).
Tsai et al., *Annu. Rev. Biochem.* 63: 451-486 (1994).
Le Goff et al., *J. Biol. Chem.* 269(6): 4458-66 (1994).
Kato et al, *Science* 270: 1491-94 (1995).
Ali et al., *EMBO J.* 12(3): 1153-60 (1993).
Joel et al., *Mol. Endocrinal.* 9(8): 1041-52 (1995).
Castano et al., *J. Steroid Biochem. Mol. Biol.* 65: 101-110 (1998).
Kobayashi et al., Breast Cancer 7(2): 136-41 (2000).
Rost et al., Steroids 65(8): 429-36 (2000).
Tyulmenkov et al., Steroids 65: 505-512 (2000).
Santa Cruz Biotechnology, Inc., Cat. No. sc-12915 (Product Description (2000).
Horwitz, *Breast Cancer Res.* 1: 5-6 (1999).
Bunone et al., *EMBO J:* 15(9): 2174-83 (1996).
Clarke et al., *J. Steroid Biochem. Mol. Biol.* 76: 71-84 (2001).
Dorssers et al., *Drugs* 61(12: 1721-33 (2001).
Chen et al., *Mol. Cell* 6(1): 127-37 (2000).
Chen et al., *Oncogene* 21: 4921-4931 (2002)—p. 4930 missing.
Sun et al., *Cancer Res.* 61(16): 5985-91 (2001).
Metzger et al., *J. Biol. Chem.* 270: 9535-542 (1995).
Kobayashi et al., *J. Biol. Chem.* 275: 15645-51 (2000).
Joel et al., *J. Biol. Chem.* 273: 13317-323 (1998).

Primary Examiner—Gary Nickol
Assistant Examiner—Audrey S. Pham
(74) Attorney, Agent, or Firm—Cell Signaling Technology, Inc.; James Gregory Cullem, Esq.; Andrew J. Warner, Esq.

(57) ABSTRACT

The invention provides monoclonal antibodies that bind the estrogen receptor α (ER α) when phosphorylated at serine 118 (Ser118) in the N-terminal domain, but do not bind to ER α when not phosphorylated at this site. Also provided are methods for determining the phosphorylation of ER α in a biological sample, profiling ER α activation in a test tissue, and identifying a compound that modulates phosphorylation of ER α in a test tissue, by using the disclosed monoclonal antibodies. The sample or test tissue may be taken from a subject suspected of having cancer, such as breast cancer. Kits comprising the phospho-ER α (Ser118) monoclonal antibodies of the invention are also provided.

4 Claims, 4 Drawing Sheets

1   mtmtlhtkas gmallhqiqg neleplnrpq lkiplerplg evyldsskpa vynypegaay
61  efnaaaaana qvygqtglpy gpgseaaafg snglggfppl nsvspsplml lhpppqlspf
121 lqphgqqvpy ylenepsgyt vreagppafy rpnsdnrrqg grerlastnd kgsmamesak
181 etrycavcnd yasgyhygvw scegckaffk rsiqghndym cpatnqctid knrrkscqac
241 rlrkcyevgm mkggirkdrr ggrmlkhkrq rddgegrgev gsagdmraan lwpsplmikr
301 skknslalsl tadqmvsall daeppilyse ydptrpfsea smmglltnla drelvhminw
361 akrvpgfvdl tlhdqvhlle cawleilmig lvwrsmehpv kllfapnlll drnqgkcveg
421 mveifdmlla tssrfrmmnl qgeefvclks iillnsgvyt flsstlksle ekdhihrvld
481 kitdtlihlm akagltlqqq hqrlaqllli lshirhmrnq gkcvegmvei fdmllatssr
541 frmmnlqgee fvclksiill nsgvytflss tlksleekdh ihrvldkitd tlihlmakag
601 ltlqqqhqrl aqlllilshi rhmsnkgmeh lysmkcknvv plydllleml dahrlhapts
661 rggasveetd qshlatagst sshslqkyyi tgeaegfpat v Figure 1: Human estrogen receptor α sequence

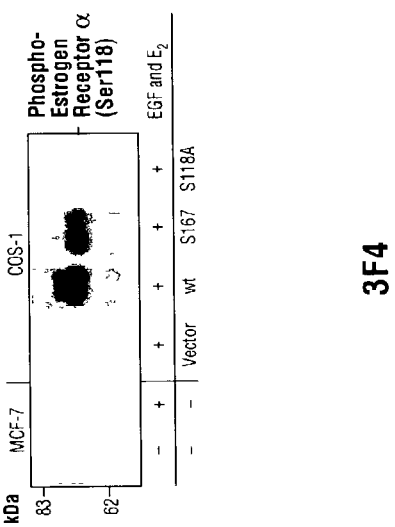
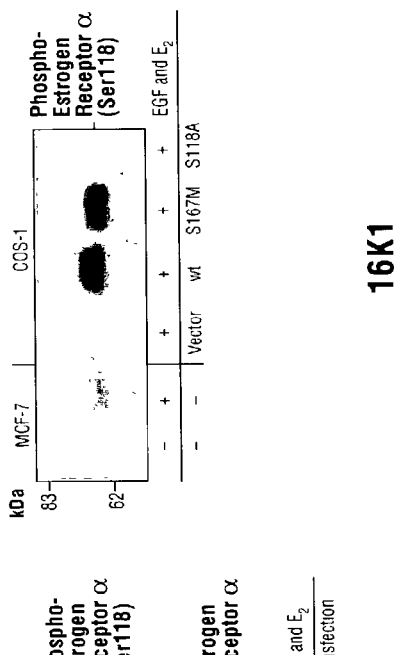
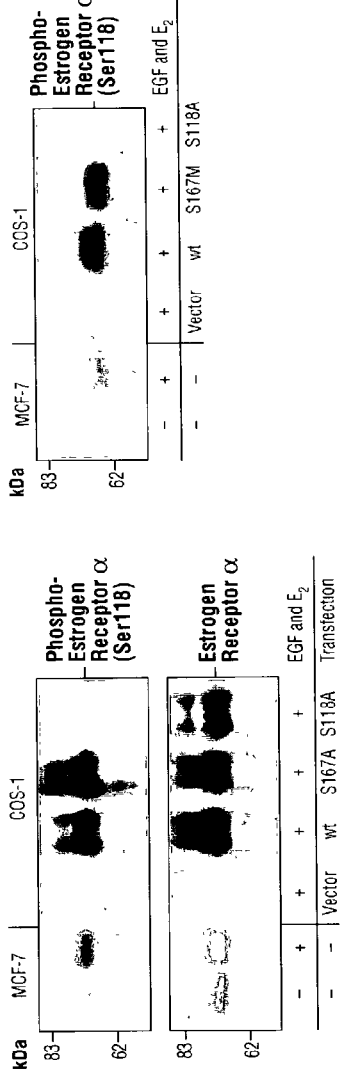
Figures 2 A-C: Western blots of extracts from MCF-7 and COS-1 cells using Phospho-Estrogen Receptor α (Ser118) Monoclonal Antibodies.

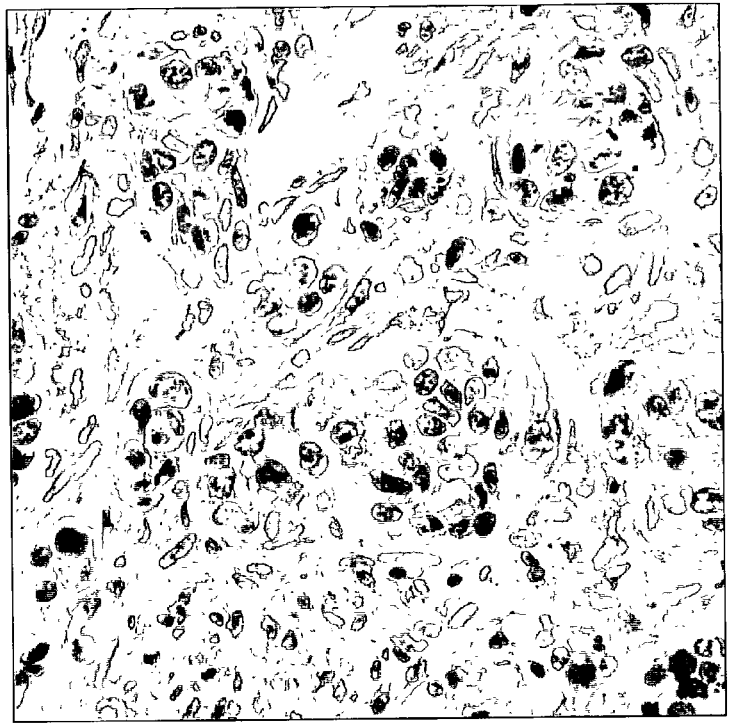
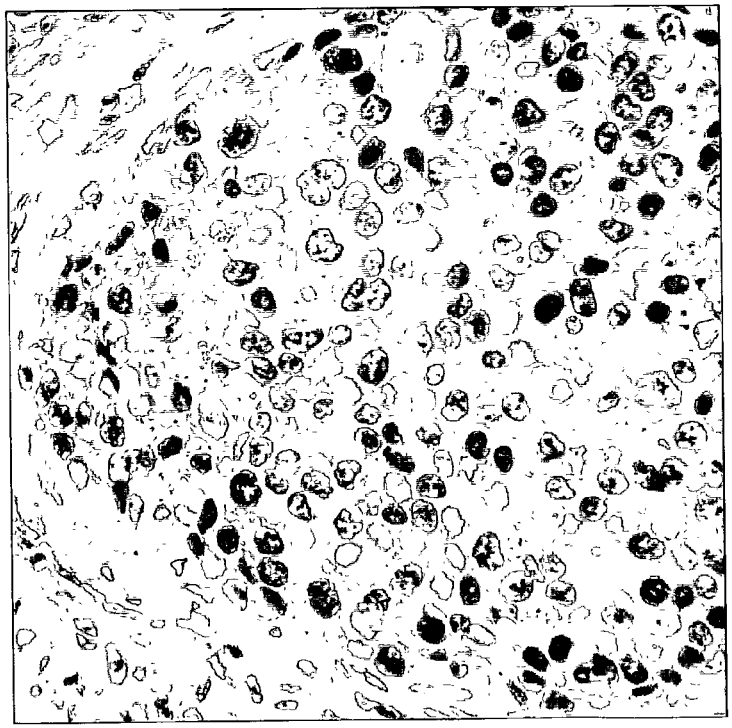
Figures 3 A-B: IHC staining of breast carcinoma tissue using Phospho-Estrogen Receptor α(Ser118) Monoclonal Antibodies.

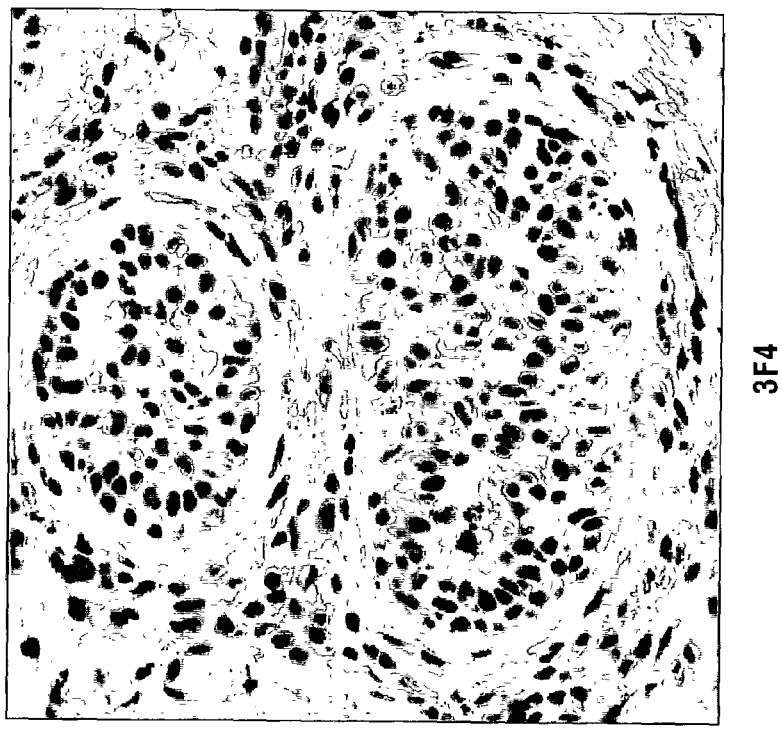
Figures 3 C: IHC staining of breast carcinoma tissue using Phospho-Estrogen Receptor α(Ser118) Monoclonal Antibodies.

SEQUENCE LISTING

<160> NUMBER OF SEQ ID NOS: 2

<210> SEQ ID NO 1
<211> LENGTH: 701
<212> TYPE: PRT
<213> ORGANISM: Homo sapiens

<400> SEQUENCE: 1

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
                35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
                115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
        370                 375                 380

Glu Ile Leu Met Ile Gly Leu Val Trp Arg Ser Met Glu His Pro Val
385                 390                 395                 400
```

```
Lys Leu Leu Phe Ala Pro Asn Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Phe Val Cys Leu
            435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Arg Asn Gln Gly Lys Cys Val Glu Gly Met Val
            515                 520                 525

Glu Ile Phe Asp Met Leu Leu Ala Thr Ser Ser Arg Phe Arg Met Met
            530                 535                 540

Asn Leu Gln Gly Glu Glu Phe Val Cys Leu Lys Ser Ile Ile Leu Leu
545                 550                 555                 560

Asn Ser Gly Val Tyr Thr Phe Leu Ser Ser Thr Leu Lys Ser Leu Glu
                565                 570                 575

Glu Lys Asp His Ile His Arg Val Leu Asp Lys Ile Thr Asp Thr Leu
            580                 585                 590

Ile His Leu Met Ala Lys Ala Gly Leu Thr Leu Gln Gln Gln His Gln
    595                 600                 605

Arg Leu Ala Gln Leu Leu Leu Ile Leu Ser His Ile Arg His Met Ser
        610                 615                 620

Asn Lys Gly Met Glu His Leu Tyr Ser Met Lys Cys Lys Asn Val Val
625                 630                 635                 640

Pro Leu Tyr Asp Leu Leu Leu Glu Met Leu Asp Ala His Arg Leu His
            645                 650                 655

Ala Pro Thr Ser Arg Gly Gly Ala Ser Val Glu Glu Thr Asp Gln Ser
                660                 665                 670

His Leu Ala Thr Ala Gly Ser Thr Ser Ser His Ser Leu Gln Lys Tyr
            675                 680                 685

Tyr Ile Thr Gly Glu Ala Glu Gly Phe Pro Ala Thr Val
            690                 695                 700

<210> SEQ ID NO 2
<211> LENGTH: 16
<212> TYPE: PRT
<213> ORGANISM: Artificial Sequence
<220> FEATURE:
<221> NAME/KEY: MOD_RES
<222> LOCATION: (12)..(12)
<223> OTHER INFORMATION: PHOSPHORYLATION; serine at position 12 is
      phosphorylated

<400> SEQUENCE: 2

Cys Leu Met Leu Leu His Pro Pro Gln Leu Ser Pro Phe Leu Gln
1               5                   10                  15
```

MONOCLONAL ANTIBODIES SPECIFIC FOR PHOSPHORYLATED ESTROGEN RECEPTOR ALPHA (SER118) AND USES THEREOF

RELATED APPLICATIONS

This application claims priority to U.S. Ser. No. 60/310,066, filed Aug. 3, 2001, now abandoned.

FIELD OF THE INVENTION

The invention relates generally to antibodies, and more particularly to antibodies to hormone receptors and their uses.

BACKGROUND OF THE INVENTION

Many cancers are characterized by disruptions in cellular signaling pathways that lead to uncontrolled growth and proliferation of cancerous cells. Receptors, including hormone receptors, play a pivotal role in these signaling pathways, transmitting extracellular molecular signals into the cytoplasm and/or nucleus of a cell. Among such receptors is the nuclear hormone receptor estrogen receptor α (ER α), which acts as a transcription factor controlling gene expression mediated by estrogen signaling.

It has long been recognized that ER α plays a central role in the development and progression of breast cancer. Breast cancer is the second most common form of cancer in women, with about 192,000 new cases annually in the United States alone. It is estimated than nearly 40,000 women will die from the disease each year (Source: American Cancer Society). More than half of all breast cancers express ER α, and about two-thirds of these cancers respond to anti-estrogen therapy, emphasizing the importance of this receptor in disease progression. See generally, Osborne er at., *Clin. Cancer* 7(12): 4338s–4342s (2001).

The transcriptional activity of ER α is mediated through two distinct domains, transcription activation functions 1 and 2 (AF-1 and AF-2), which can act either independently or synergistically, in a promoter- or cell-dependent manner. See, e.g. Beato et al. *Cell* 83: 851–857 (1995); Tsai et al., *Annu. Rev. Biochem.* 63: 451–486 (1994). While estrogen binding controls AF-2 transcriptional activity, it has been shown that phosphorylation of ER α at one of three sites (serine 104 and/or 106,118, and/or 167) in the 180 amino acid N-terminal domain comprising AF-1 mediates the estrogen-independent transcriptional activity of this domain. See e.g. Le Goff et al., *J. Biol. Chem.* 269(6): 4458–66 (1994). In particular, phosphorylation of serine 118, which can occur via the MAPK pathway, has been shown to be critical for the AF-1 activity of ER α. See, e.g. Kato et al., *Science* 270: 1491–94 (1995); Ali et al., *EMBO J.* 12(3): 1153–60 (1993); Joel et al., *Mol. Endocrinol.* 9(8): 1041–52 (1995); Castano et al. *J. Steroid Biochem. Mol. Biol.* 65: 101–110 (1998). Antibodies to ER α have been described (see, e.g. Kobayashi et al., *Breast Cancer* 7(2): 136–41 (2000); Rost et al., *Steroids* 65(8): 429–36 (2000); Tyulmenkov et al., *Steroids* 65: 505–512 (2000)), and a phospho-specific polyclonal antibody to ER α (Ser118) is commercially available (Santa Cruz Biotechnology, Inc., Cat. No. sc-12915).

Given the prevalence of ER α activation in breast cancers, this receptor has long been a target for inhibitory therapies. Tamoxifen, a systemic ER inhibitor (acting to suppress AF-1 activity), has been the therapy of choice for ER-positive breast cancer for many decades. More recently, second-generation inhibitors, such as raloxifene, have entered clinical development. Unfortunately, although about fifty percent of patients with advance ER-positive breast cancer initially respond to tamoxifen therapy, the disease ultimate acquires tamoxifen-resistance through mechanisms that are not presently well understood. See, e.g. Horwitz, *Breast Cancer Res.* 1: 5–6 (1999). Despite the lack of a clear mechanism of tamoxifen-resistance, it has been postulated that steroid-independent phosphorylation of ER mutants may be a contributing factor. Bunone et al. *EMBO J.* 15(9): 2174–83 (1996). More recent reports indicate that acquisition of tamoxifen-resistance in ER-positive breast cancer is likely to involve multiple, interrelated signaling pathways in an estrogen-independent manner. See, e.g. Clarke et al., *J. Steroid Biochem. Mol. Biol.* 76: 71–84 (2001); Dorssers et al., *Drugs* 61(12): 1721–33 (2001). Indeed, it has been reported that the efficient phosphorylation of ER α at serine 118 requires a ligand-regulated interaction between CDK and AF-2. See, e.g. Chen et al., *Mol. Cell* 6(1):127–37 (2000).

Accordingly, given the importance of ER α in breast cancer progression, there remains a need for new and improved reagents, such as monoclonal antibodies, capable of specifically detecting phosphorylation (and hence, activation) of ER α at serine 118. Since phosphorylation-dependent activation of ER α is associated with diseases such as breast cancer, reagents enabling the specific detection of ER α activation would be useful tools for research and clinical applications. ER α (Ser118)-specific monoclonal antibodies would be desirable for studying the mechanisms of resistance to therapeutics like tamoxifen, as well as for applications, such as diagnostic assays, where reagent purity and consistency are paramount.

SUMMARY OF THE INVENTION

The invention provides monoclonal antibodies that bind to estrogen receptor α (ER α) only when it is phosphorylated at serine 118 (Ser118) in the N-terminal domain (corresponding to AF-1 activity). The monoclonal antibodies do not bind to ER α when it is not phosphorylated at this site nor do they bind to other hormone receptors. The invention also provides hybridoma clones producing the phospho-ER α (Ser118) monoclonal antibodies disclosed. Also provided are methods of determining the phosphorylation of ER α in a biological sample, profiling ER α activation in a test tissue, and identifying a compound that modulates phosphorylation of ER α in a test tissue, by using the disclosed phospho-ER α (Ser118) antibodies. The sample or test tissue may be taken from a subject suspected of having cancer, and the antibody used to determine the patient's potential or actual response (or resistance) to cancer therapies, such as tamoxifen, targeted at ER α and/or related signaling pathways.

BRIEF DESCRIPTION OF THE DRAWINGS

This patent or application file contains at least one drawing executed in color. Copies of this patent or patent application publication with color drawing(s) will be provided by the United States Patent Office upon request and payment of the necessary fee.

FIG. 1—is the amino acid sequence (1-letter code) of human, ER α (SEQ ID NO: 1). Residues 1 to 150 comprise the N-terminal domain encoding the AF-1 activity. The peptide sequence used comprised in the immunogen (residues 108–122) is indicated in bold, serine 118 being underlined.

FIGS. 2A–C—are Western blot analyses using the phospho-ER α (Ser118) monoclonal antibodies of the invention (CST #16J4 in FIG. 2A; CST #16K1 in FIG. 2B; CST #3F4 in FIG. 2C) on extracts of MCF7 cells and COS-1 cells transfected with wild-type or mutant (at Ser118 or Ser167) ER α stimulated with EGF and $E_2$ or β-estradiol. For comparison, the lower panel of FIG. 2A shows the same lysates (for #16J4) probed with an anti-ER α control antibody that reacts equally with the phospho and the non-phospho proteins.

FIGS. 3A–C—are immunohistochemical (IHC) analyses of paraffin-embedded human breast carcinoma tissue probed with the phospho-ER α (Ser118) monoclonal antibodies of the invention (CST #16J4 in FIG. 3A; CST #16K1 in FIG. 3B; CST#3F4 in FIG. 3C) showing positive nuclear membrane staining of tumor cells.

DETAILED DESCRIPTION OF THE INVENTION

In accordance with the present invention there are provided monoclonal antibodies that binds to ER α only when it is phosphorylated at serine 118 (Ser118) in the N-terminal domain (which encodes the AF-1 activity) (see FIG. 1). Phosphorylation at this site is of particular interest as it has been shown to regulate the estrogen-independent AF-1 transcriptional activity of ER α, which activity is believed to be a key step in breast tumor progression. See, e.g. Kato et al., supra. Recent reports indicate that serine 118 phosphorylation is mediated by various signaling pathways, including the mitogen-activated protein kinase (MAPK), cyclin-dependent protein kinase 7 (Cdk7), and phosphatidylinositol-3-OH (Pl3K)/AKT2 pathways. See Chen et al., Oncogene 21: 4921–4931 (2002); Sun et al., Cancer Res. 61(16): 5985–91 (2001). Therefore, detection of phosphorylation at this site in ER α is an important indication of the molecular events that have given rise to a particular cancer. Detection of the phosphorylation of ER α at Ser118 may also provide valuable information about the mechanisms of resistance to ER-inhibitors, such as tamoxifen. The invention also provides hybridoma clones producing the disclosed phospho-ER α (Ser118) monoclonal antibodies.

Also provided are methods of using the monoclonal antibody of the invention to detect ER α phosphorylation and activation in a biological sample or test tissue suspected of containing phosphorylated ER α or having altered ER α activity, as further described below. All references cited above and below are hereby incorporated herein by reference.

A. Antibodies and Cell Lines

The invention provides ER α phosphospecific monoclonal antibodies (CST #16J4, #16K1, and #3F4) that selectively bind to ER α only when phosphorylated at Ser118 in the N-terminal domain, but does not substantially bind to ER α when not phosphorylated at this residue, nor to ER α when phosphorylated at other residues. The antibodies do not bind other hormone receptors, e.g. ER β. The ER α N-terminal domain, which encodes the estrogen-independent AF-1 transcriptional activity of the protein, is composed of 150 amino acids, including a hydrophobic proline-rich subdomain (residues 51–149). See Metzger et al., J. Biol. Chem. 270: 9535–542 (1995); Kobayashi et al., J. Biol. Chem. 275: 15645–51 (2000); see also FIG. 1.

The ER α antibodies of the invention include the monoclonal antibodies CST #16J4, #16K1, and #3F4, which bind phospho-ER α (Ser118), and fragments of these antibodies which bind to the antigen (or more preferably the epitope) bound by the monoclonal antibody disclosed herein. Such antibodies and antibody fragments may be produced by a variety of techniques well known in the art, as discussed below. Antibody fragments that bind to the phosphorylated epitope (i.e., the specific binding site) bound by the ER α (Ser118) antibodies disclosed herein can be identified in accordance with known techniques, such as their ability to compete with labeled monoclonal antibody in a competitive binding assay.

The preferred epitopic site of the ER α (Ser118) antibodies of the invention is a peptide fragment consisting essentially of about 11 to 17 amino acids including the phosphorylated serine 118, wherein about 4 to 8 amino acids are positioned on each side of the serine phosphorylation site (for example, residues 108–122 of ER α (see FIG. 1; SEQ ID NO: 1).

The term "antibody" or "antibodies" as used herein refers to all types of immunoglobulins, including IgG, IgM, IgA, IgD, and IgE. The antibody may be of any species of origin, including (for example) mouse, rat, rabbit, horse, or human, or may be chimeric antibodies. See, e.g., M. Walker et al., Molec. Immunol. 26: 403–11 (1989); Morrision et al., Proc. Nat'l. Acad. Sci. 81: 6851 (1984); Neuberger et al., Nature 312: 604 (1984). The monoclonal antibody may be a recombinant monoclonal antibody produced according to the methods disclosed in U.S. Pat. No. 4,474,893 (Reading) or U.S. Pat. No. 4,816,567 (Cabilly et al.). The antibodies may also be chemically constructed by specific antibodies made according to the method disclosed in U.S. Pat. No. 4,676, 980 (Segel et al.) The term "ER α antibody" means a monoclonal antibody that binds phospho-ER α (Ser118), as disclosed herein. The term "does not bind" with respect to such an antibody means does not substantially react with as compared to binding to phospho-ER α.

Monoclonal antibodies of the invention may be produced in a hybridoma cell line according to the well-known technique of Kohler and Milstein. Nature 265: 495–97 (1975); Kohler and Milstein, Eur. J. Immunol. 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in Escherichia coli by recombinant techniques known to those skilled in the art. See, e.g., W. Huse, Science 246: 1275–81 (1989); Mullinax et al., Proc. Nat'l Acad. Sci. 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods,* 74: 307 (1984)).

The invention also provides hybridoma clones, constructed as described above, that produce an ER α monoclonal antibody of the invention. In a preferred embodiment, the phospho-ER α (Ser118) monoclonal antibody of the invention is monoclonal antibody CST #16J4 produced by clone 16-J4, CST #16K1 produced by clone 16-K1, or CST #3F4 produced by clone 3-F4. Similarly, the invention includes recombinant cells producing an ER α monoclonal antibody as disclosed herein, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor).

Samples of hybridomas 16-J4, 16-K1, and 3-F4 producing monoclonal antibodies of the invention were deposited with the American Type Culture Collection, in accordance with the Budapest Treaty, on Aug. 21, 2001, and received Patent Deposit Nos. PTA-3606, PTA-3607, and PTA-3608, respectively.

ER α antibodies of the invention may be screened for epitope and phospho-specificity according to standard techniques. See, e.g. Czernik et al., *Methods in Enzymology,* 201: 264–283 (1991). For example, the antibodies may be screened against the phospho and non-phospho peptide library by ELISA to ensure specificity for both the desired antigen (i.e. that epitope including Ser118) and for reactivity only with the phosphorylated form of the antigen. Peptide competition assays may be carried out to confirm lack of reactivity with other ER α phospho-epitopes. The antibodies may also be tested by Western blotting against cell preparations containing ER α, e.g. cell lines over-expressing ER α, to confirm reactivity with the desired phosphorylated target. Specificity against the desired phosphorylated epitopes may also be examined by construction ER α mutants lacking phosphorylatable residues at positions outside the desired epitope known to be phosphorylated, or by mutating the desired phospho-epitope and confirming lack of reactivity. ER α antibodies of the invention may exhibit some cross-reactivity with non-ER α epitopes. This is not unexpected as many enzymes are highly homologous at key regulatory serine sites and antibodies will often cross-react with epitopes having high homology to the immunizing peptide. See, e.g., Czernik, supra. Cross-reactivity with non-ER α proteins is readily characterized by Western blotting alongside markers of known molecular weight. Amino acid sequences of cross-reacting proteins may be examined to identify sites highly homologous to the ER α sequence surrounding serine 118.

ER α monoclonal antibodies may be further characterized via immunohistochemical (IHC) staining using normal and diseased tissues to examine ER α phosphorylation and activation status in diseased tissue. IHC may be carried out according to well known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

B. Detection & Profiling Methods

The methods disclosed herein may be employed with any biological sample suspected of containing phosphorylated ER α. Phosphorylation of ER α at serine 118, along with other residues, is necessary for the estrogen-independent transcriptional activity of the receptor (see, e.g. Kato et al., supra.; Castano et al., supra.). Biological samples taken from human subjects for use in the methods disclosed herein are generally biological fluids such as serum, blood plasma, fine needle aspirant, ductal lavage, bone marrow sample, or ascites fluid. In the alternative, the sample taken from the subject can be a tissue sample (e.g., a biopsy tissue), such as skin or hair follicle or tumor tissue.

In one embodiment, the invention provides a method for detecting phosphorylated ER α in a biological sample by (a) contacting a biological sample suspected of containing phosphorylated ER α with a phospho-ER α (Ser118) monoclonal antibody under conditions suitable for formation of an antibody-ER α complex, and (b) detecting the presence of the complex in the sample, wherein the presence of the complex indicates the presence of phosphorylated ER α (Ser118) in the sample. Biological samples may be obtained from subjects suspected of having a disease involving altered ER α expression or activity (e.g., breast cancer). Samples may be analyzed to monitor subjects who have been previously diagnosed as having cancer, to screen subjects who have not been previously diagnosed as carrying cancer, or to monitor the desirability or efficacy of therapeutics targeted at ER α (e.g. tamoxifen). In the case of breast cancer, for example, the subjects will most frequently be females.

In another embodiment, the invention provides a method for profiling ER α activation in a test tissue suspected of involving altered ER α activity, by (a) contacting the test tissue with a phospho-ER α (Ser118) monoclonal antibody under conditions suitable for formation of an antibody-ER α complex, (b) detecting the presence of the complex in the test tissue, wherein the presence of the complex indicates the presence of phosphorylated ER α (Ser118) in the test tissue, and (c) comparing the presence of phosphorylated ER α detected in step (b) with the presence of phosphorylated ER α in a control tissue, wherein a difference in ER α phosphorylation profiles between the test and control tissues indicates altered ER α activation in the test tissue. In a preferred embodiment, the test tissue is a cancer tissue, such as a breast cancer tissue, suspected of involving altered ER α Ser118 phosphorylation.

The methods described above are applicable to examining tissues or samples from cancers characterized by ER α activity, such as breast cancers, in which phosphorylation of ER α at Ser118 has predictive value as to the progression or outcome of the disease or the response of the disease to targeted therapy. It is anticipated that the monoclonal antibodies of the invention will have diagnostic utility in diseases characterized by, or involving, altered ER α activity or altered ER α Ser118 phosphorylation. The methods are applicable, for example, where samples are taken from a subject that has not been previously diagnosed as having breast cancer, nor has yet undergone treatment for breast cancer, and the method is employed to help diagnose the disease, or monitor the possible progression of the cancer, or assess risk of the subject developing such cancer involving ER α (Ser118) phosphorylation. Such diagnostic assay may be carried out prior to preliminary blood, skin biopsy evaluation or surgical surveillance procedures. Such a diagnostic assay may be employed to identify patients with activated ER α who would be most likely to respond to cancer therapeutics targeted at inhibiting ER α activity. Such a selection of patients would be useful in the clinical evaluation of efficacy of future ER α inhibitors as well as in the future prescription of such drugs to patients. Alternatively, the methods are applicable where a subject has been previously diagnosed as having breast cancer, and possibly has already undergone treatment for the disease, and the method is employed to monitor the progression of such cancer involving ER α (Ser118) phosphorylation, or the treatment thereof.

In another embodiment, the invention provides a method for identifying a compound which modulates phosphorylation of ER α in a test tissue, by (a) contacting the test tissue with the compound, (b) detecting the level of phosphorylated ER α in said test tissue of step (a) using a phospho-ER α (Ser118) monoclonal antibody under conditions suitable for formation of an antibody-ER α complex, and (c) comparing the level of phosphorylated ER α detected in step(b) with the presence of phosphorylated ER α in a control tissue not contacted with the compound, wherein a difference in ER α phosphorylation levels between the test and control tissues identifies the compound as a modulator of ER α phosphorylation. In preferred embodiments, the test tissue is a taken from a subject suspected of having cancer, e.g. breast cancer, and the compound is a ER α inhibitor. The compound may modulate ER α activity by either positively or negatively, for example by increasing or decreasing phosphorylation or expression of ER α. ER α phosphorylation and activity may be monitored, for example, to determine the efficacy of an anti-ER α therapeutic, e.g. a ER α inhibitor such as tamoxifen or raloxifene.

Conditions suitable for the formation of antibody-antigen complexes or reagent-ER α complexes are well known in the art (see part (d) below and references cited therein).

Phospho-ER α (Ser118) monoclonal antibodies of the invention will be useful in profiling the molecular mechanisms underlying patient resistance to ER α inhibitors, such as tamoxifen. Since resistance to such inhibitors is likely to be a result of multiple signal transduction pathway events (see Clarke et al., supra.; Dorssers et al., supra.), p-ER α antibodies of the invention will be of value in examining the activation of ER α in response to upstream signaling events in related pathways.

D. Immunoassay Formats & Diagnostic Kits

Assays carried out in accordance with methods of the present invention may be homogeneous assays or heterogeneous assays. In a homogeneous assay the immunological reaction usually involves an ER α monoclonal antibody of the invention, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, the ER α antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof which may be useful for carrying out the methods disclosed herein are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of phosphorylated ER α is detectable compared to background.

p-ER α antibodies disclosed herein may be conjugated to a solid support suitable for a diagnostic assay (e.g., beads, plates, slides or wells formed from materials such as latex or polystyrene) in accordance with known techniques, such as precipitation. Antibodies of the invention, or other ER α binding reagents, may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

p-ER α monoclonal antibodies of the invention may also be used in a flow cytometry assay to determine the activation status of ER α in patients before, during, and after treatment with a drug targeted at inhibiting ER α phosphorylation at Ser118. For example, fine needle aspirants from ductal ravages or dispersed solid tumor biopsies from patients may be analyzed by flow cytometry for ER α phosphorylation, as well as for markers identifying various epithelial cell types. In this manner, ER α activation status of the malignant cells may be specifically characterized. Flow cytometry may be carried out according to standard methods. See, e.g. Chow et al., Cytometry (Communications in Clinical Cytometry) 46: 72–78 (2001). Briefly and by way of example, the following protocol for cytometric analysis may be employed: fixation of the cells with 2% paraformaldehyde for 20 minutes at 37° C. followed by permeabilization in 90% methanol for 30 minutes on ice. Cells may then be stained with the primary p-ER α antibody, washed and labeled with a fluorescent-labeled secondary antibody. The cells would then be analyzed on a flow cytometer (e.g. a Beckman Coulter EPICS-XL) according to the specific protocols of the instrument used. Such an analysis would identify the presence of activated ER α in the malignant cells and reveal the drug response on the targeted ER α protein.

Diagnostic kits for carrying out the methods disclosed above are also provided by the invention. Such kits comprise at least one ER α (Ser118) monoclonal antibody of the invention. In a preferred embodiment, there is provided a kit for the detection of phosphorylated ER α in a biological sample comprising (a) a phospho-ER α (Ser118) antibody of the invention and (b) a secondary antibody conjugated to a detectable group. In a preferred embodiment, the antibody of the invention is may be coupled to a solid support. The reagents may also include ancillary agents such as buffering agents and protein stabilizing agents, e.g., polysaccharides and the like. Diagnostic kits may further include, where necessary, other members of the signal-producing system of which system the detectable group is a member (e.g., enzyme substrates), agents for reducing background interference in a test, control reagents, apparatus for conducting a test, and the like. In another embodiment, a test kit comprises (a) a phospho-ER α (Ser118) antibody as described herein, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test.

The following examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Production of ER α Ser118 Phosphospecific Monoclonal Antibodies

Monoclonal antibodies of the invention were produced by immunizing BALB/C mice with the following peptide: CLMLLHPPPQLS*PFLQ (SEQ ID NO: 2), where S*=phosphoserine at position 118 of the ER α sequence (see FIG. 1). This sequence comprises residues 108 to 122 of human ER α with a cysteine on the N-terminal. Mice were immunized with 50 μg/200 μl of this peptide in Complete Freund's Adjuvant, via intraperitoneal injection (IP). After three weeks, mice were further immunized with 25 μg/100 μl of the peptide in Incomplete Freund's Adjuvant (IFA), via IP. Four weeks post second injection, mice were further immunized with 12.5 μg/50 μl of the peptide in IFA, via IP. Three-and-one-half-months after the third injection, one animal, mouse #248D, was selected and further immunized with 12.5 μg/50 μl of the peptide in sterile phosphate buffered saline, via intravenous injection in the tail vein.

Hybridomas were prepared according to standard techniques. See Harlow et al., "Antibodies: A Laboratory Manual," Cold Spring Harbor Laboratory 1988, pp. 274–275. Briefly, SP2/0 myeloma cells were expanded in DMEM+10% Hyclone serum with L-gluatmine, penicillin/streptomycin, gentamycin, sodium pyruvate, β-ME, and fungizone (medium A). The cells were harvested from T-175 tissue culture flasks, and spun in a centrifuge to form a pellet, which was washed twice with DMEM. Spleen was excised from mouse #248D after a day −3 I.V. boost with the immunizing peptide, and splenocytes were flushed from the spleen into a sterile petri dish using DMEM and an 18 gauge needle attached to a 5 mL syringe. The flushed contents of the spleen were drawn into the needleless syringe, then expelled to break up small pieces of tissue. Splenocytes were combined with washed myeloma cells. The petri dish was washed once with 10 mL DMEM, and the wash added to the combined cells, and then spun. Combined cell pellet was washed once with DMEM. After aspirating the supernatant, the pellet was gently agitated with a tapping motion.

1 mL of PEG 1500 was added drop-wise to the cell pellet over the span of a minute, mixing after addition of each drop. The suspension was mixed for an additional two minutes, then 4 mL of DMEM were added drop-wise over the course of five minutes. The suspension was incubated at room temperature for five minutes, then 45 mL of Medium A were added slowly to neutralize the PEG. The suspension was spun, then washed with DMEM. The fused cells were resuspended in 99 mL of DMEM +20% Hyclone serum with penicillin/streptomycin, gentamycin, sodium pyruvate, β-ME, and fungizone, O.P.I. supplement, IL-6, and HT supplement (medium E). To this mixture, 1 mL of 100× HAT supplement was added, and the mixture was plated into 10 96-well tissue culture treated plates, 100 μL/well.

On days 7, 9, and 11 post-fusion, the contents of each well was aspirated and replaced with 100 μL fresh medium E. On day 12, the fusions were screened by ELISA, as follows: 50 μL supernatant were removed from each well and transferred into corresponding wells on 96-well microtiter plates pre-coated with the immunizing peptide (SEQ ID NO: 2). Antibodies binding phospho-ER α were detected by addition of AP linked a-mouse IgG, then 1 mg/mL p-nitrophenyl phosphate substrate solution. 66 positive wells were detected, and the cells growing in the corresponding tissue culture plates were expanded and tested for ELISA reactivity as described above.

Of the 66 initial positives, 21 samples remained positive on secondary screening. These 21 samples were tested by Western blot on MCF-7 (a breast carcinoma cell line) cells untreated or stimulated with estradiol, the ER ligand, in order to induce phosphorylation of ER α. Seven samples showed enhanced reactivity with the induced cells; all seven were subcloned. After three rounds of subcloning, three single clones, 16-J4, 16-K1, and 3-F4 were isolated.

Confirmation of Specificity

Monoclonal antibodies produced by the three isolated clones were tested for phospho-ER α (Ser118) specificity by Western blot screening against recombinant ER with mutations at various phosphorylation sites (see FIGS. 2A–2C). The results demonstrate that the monoclonal antibodies are specific for phosphorylation at the serine 118 residue. The antibodies do not recognize phosphorylation at other residues such as the serine 104/106 or serine 167 sites. The reactivity is not seen if the serine 118 site is mutated to an alanine, preventing phosphorylation at that site. Thus, clones 16-J4, 16-K1, and 3-F4 were confirmed as producing monoclonal antibodies (CST #16J4, #16K1, and #3F4) having the desired p-ER (Ser118) specificity.

EXAMPLE 2

Detection of ER α Phosphorylation In Immunohistochemical Analysis of Human Breast Tumor Tissue Immunohistochemical (IHC) analysis of paraffin-embedded tumor samples is the most common method for analyzing the pathology of a tumor. Determining the molecular pathology of the tumor may also be obtained through an IHC analysis of paraffin-embedded tissues. New cancer therapies targeted at the ER α receptor require that the patient have the ER α receptor and that the receptor is activated. Therefore, phospho-ER α (Ser118) monoclonal antibodies of the invention may be used to prescreen patients for inclusion in a clinical trial or before treatment with an ER α inhibitor, such as tamoxifen.

For IHC analysis, tissue acquisition, paraffin-embedding and sectioning were performed by Newcomer Supply, Middleton, WI. The obtained tissue sections were de-paraffinized with xylene and ethanol, then microwaved for 13 minutes in a 10 mM sodium citrate pH 6.0 buffer for antigen unmasking. After a 10 minute incubation in 3.0% H2O2, the sections were blocked in 5% goat serum for 1 hour. The slides were then stained with phospho-ER α (Ser118) monoclonal antibody #16J4, #16K1, or #3F4, respectively, overnight at 4° C. After 3 washes in PBS, the slides were probed with a secondary antibody labeled with biotin, washed again 3 times, then the slides were incubated with an avidin-biotin-HRP reagent (ABC kit) following standard manufacturer procedures. The slides were developed using a HRP substrate, either DAB or NovaRed™ and counterstained with hematoxylin. Positive staining for Phospho-ER α was scored based upon staining intensity, number of cells stained and nuclear localization of stain.

The results of the immunohistochemical analysis on breast tumor sections shows strong nuclear staining of malignant epithelial cells as predicted for breast carcinomas in which ER α is activated (see FIGS. 3A–C). This result indicates the utility of monoclonal antibodies of the invention in detection of ER α activation in vivo.

EXAMPLE 3

Tissue Microarray Analysis of Estrogen Receptor Serine 118 Phosphorylation and Correlations to Pathological Indices A phosphorylation-specific ER α (Ser118) monoclonal antibody of the invention was used in a tissue array analysis to determine if phosphorylation at this residue correlated with any pathological indices such as tumor grade, tumor stage (pn and pt), lymph node status or nuclear status (mitoses). Tissue arrays provide a rapid method to screen a large number of patient samples under uniform conditions identical for all sections. In this experiment a breast tumor array consisting of 62 sections, each taken from a single patient, was analyzed. The corresponding pathological indices were also known for each patient.

The array was probed with the monoclonal antibody (clone 16J4) under standard immunohistochemical conditions as described above (see e.g. ANTIBODIES: A LABORATORY MANUAL, Chapter 10, supra.) and scored according to nuclear staining intensity and percentage of cells stained. The tissue array was constructed following standard tissue embedding techniques including formalin fixation and paraffin embedding. The results were compared to the pathological indices by calculating Pearson Correlation coefficients. A significant correlation would suggest that estrogen receptor phosphorylation may be playing a significant role in the pathology of a tumor. Correlation coefficients to activation of other pathways such as the MAP kinase pathway and the AKT pathway were also calculated, in order to examine whether estrogen receptor serine 118 phosphorylation was linked to activation of these other pathways.

The results of the tissue array analysis and correlation calculations are shown below in Table 1. The level of significance for P≦0.05 is 0.27 and is marked on the figure by a solid line.

TABLE 1

Correlation Coefficients for Estrogen Receptor Serine 118 Phosphorylation

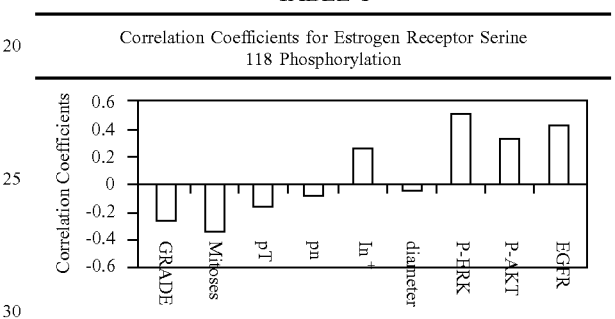

These correlation results indicate that ER α phosphorylation at serine 118 is negatively correlated with tumor grade and tumor mitoses and positively correlated with number of positive lymph nodes. These results support the conclusion that ER α (Ser118) phosphorylation may play a role in tumor progression and metastases. The analysis also demonstrates that phosphorylation at serine 118 correlates with erk (MAP kinase) and AKT activation. The highest correlation is with erk activation. The erk or MAP kinase pathway is one of the pathways that is directly responsible for serine 118 phosphorylation. See, e.g. Chen et al., supra. The correlation with AKT is not unexpected, as shown by the correlation with EGFR expression. Over-expression of the EGF receptor is predicted to activate both the erk and the AKT pathways in many tumors. Accordingly, a correlation with serine 118 phosphorylation would be predicted.

These results demonstrate that estrogen receptor a phosphorylation at serine 118 detected with this monoclonal antibody is predictive of pathway activation in breast tumors and may be useful in clinical applications to profile patient pathway activation for the purpose of prescribing targeted therapeutics.

What is claimed is:

1. A monoclonal antibody that specifically binds to estrogen receptor α (ERα) when phosphorylated at Serine 118 in the N-terminal domain (residues 1 to 150) of SEQ ID NO: 1, but does not bind to ERα when not phosphorylated at this position, wherein said antibody is produced by hybridoma cell line ATCC Accession No. PTA-3606, PTA-3607, or PTA-3608.

2. A hybridoma cell line producing the monoclonal antibody of claim 1.

3. A method for detecting phosphorylated ERα at Serine 118 in a biological sample, said method comprising the steps of:
 (a) contacting a biological sample suspected of containing phosphorylated ERα with the monoclonal antibody of claim 1 under conditions suitable for formation of an antibody-antigen complex; and
 (b) detecting the presence of said complex in said sample, wherein the detection of said complex indicates the presence of phosphorylated ERα (Ser118) in said sample.

4. A kit for the detection of phosphorylated ERα in a biological sample, said kit comprising (a) at least one phospho-ERα (Set118) monoclonal antibody of claim 1 and (b) at least one secondary antibody conjugated to a detectable group.

* * * * *